US012642621B2

(12) United States Patent
Krause et al.

(10) Patent No.: US 12,642,621 B2
(45) Date of Patent: Jun. 2, 2026

(54) IMPLANTABLE MARKER BODY FOR BREAST TREATMENT

(71) Applicant: SOMATEX MEDICAL TECHNOLOGIES GMBH, Berlin (DE)

(72) Inventors: Thorsten Krause, Berlin (DE); Nils Drewes, Berlin (DE); Sophie Melzer, Berlin (DE); Dirk Hornscheidt, Berlin (DE); Jonathan Cornelius Berndt, Berlin (DE); Merlin Bergmeister, Berlin (DE)

(73) Assignee: SOMATEX MEDICAL TECHNOLOGIES GmbH, Berlin (DE)

( * ) Notice: Subject to any disclaimer, the term of this patent is extended or adjusted under 35 U.S.C. 154(b) by 155 days.

(21) Appl. No.: 17/797,984

(22) PCT Filed: Feb. 5, 2021

(86) PCT No.: PCT/EP2021/052864
§ 371 (c)(1),
(2) Date: Aug. 5, 2022

(87) PCT Pub. No.: WO2021/156474
PCT Pub. Date: Aug. 12, 2021

(65) Prior Publication Data
US 2023/0038320 A1     Feb. 9, 2023

(30) Foreign Application Priority Data
Feb. 6, 2020     (DE) .................... 10 2020 000 762.7

(51) Int. Cl.
*A61B 90/00*     (2016.01)
*A61L 31/06*     (2006.01)
(Continued)

(52) U.S. Cl.
CPC .............. *A61B 90/39* (2016.02); *A61L 31/06* (2013.01); *A61L 31/18* (2013.01); *A61N 5/1049* (2013.01);
(Continued)

(58) Field of Classification Search
CPC .. A61B 2017/00004; A61B 2090/3991; A61B 90/39; A61B 2090/3966;
(Continued)

(56) References Cited

U.S. PATENT DOCUMENTS

| | | | |
|---|---|---|---|
| 6,340,367 B1 * | 1/2002 | Stinson ...................... | A61F 2/90 |
| | | | 623/1.34 |
| 6,722,371 B1 * | 4/2004 | Fogarty .................. | A61B 90/39 |
| | | | 606/116 |

(Continued)

FOREIGN PATENT DOCUMENTS

| | | | | |
|---|---|---|---|---|
| CN | 110037756 A | * | 7/2019 | ............. A61B 17/00 |
| WO | 2001008578 | | 2/2001 | |
| WO | WO-0108578 A1 | * | 2/2001 | ............. A61B 90/39 |

OTHER PUBLICATIONS

International Search Report and Written Opinion for PCT/EP2021/052864 dated May 3, 2021, 13 pages.

*Primary Examiner* — Oommen Jacob
(74) *Attorney, Agent, or Firm* — Jones Burke, PLLC

(57) ABSTRACT

The invention relates to a marker body (10) for marking breast tissue for radiotherapy. The marker body (10) has an at least partly tube-like body (12) which is made from a soft elastic material and carries multiple radio-opaque marker elements (18). The at least partly tube-like body (12) is designed so that it offers hardly any resistance to an external, deforming force, but returns to its original shape in the absence of external forces. The at least partly tube-like body (12) has two free longitudinal ends (14, 16) which can be
(Continued)

Figure 1:
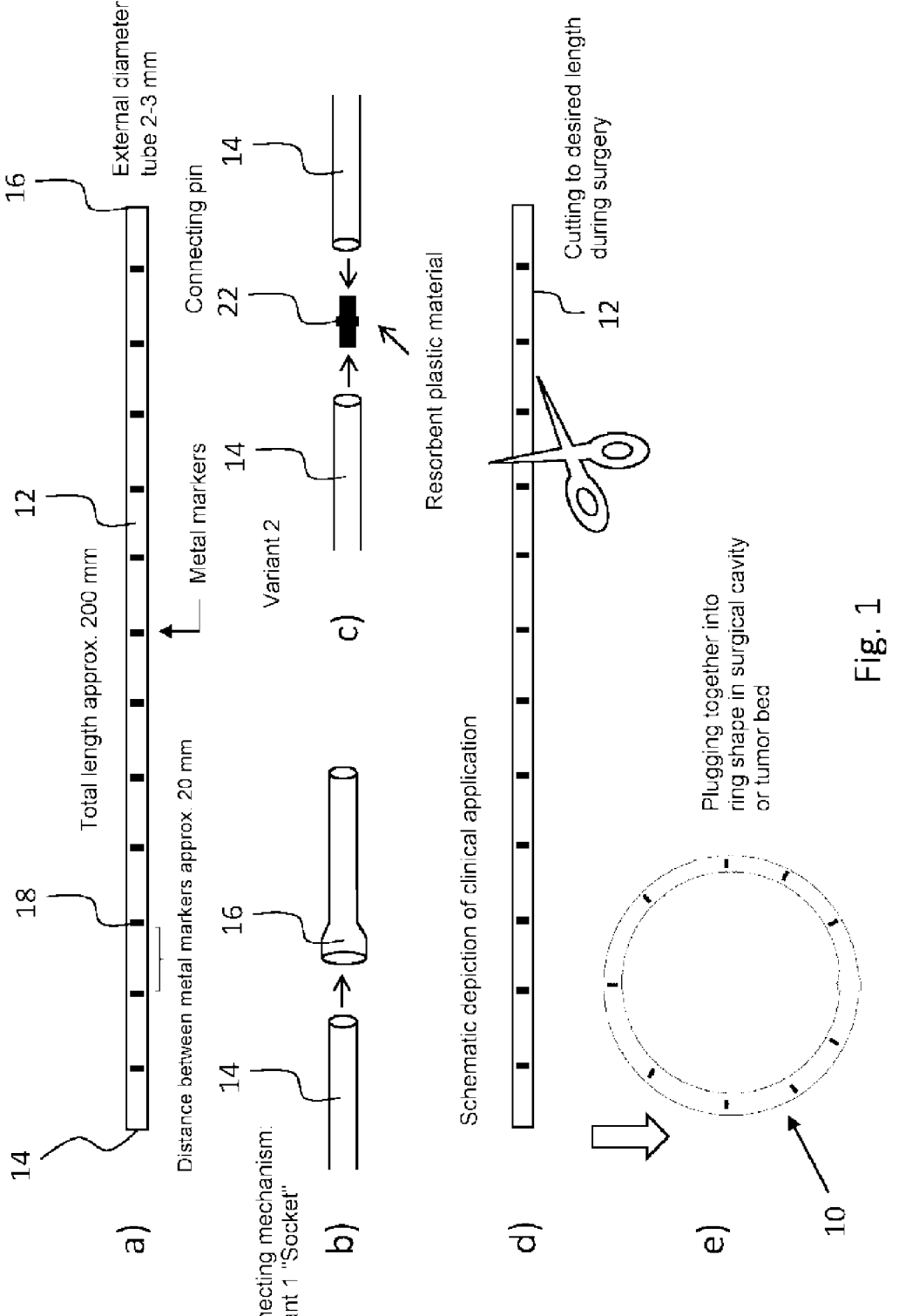

detachably interconnected or are interconnected, resulting in a tubular ring.

25 Claims, 22 Drawing Sheets

(51) Int. Cl.
  *A61L 31/18*          (2006.01)
  *A61N 5/10*          (2006.01)
(52) U.S. Cl.
  CPC ................. *A61B 2090/3908* (2016.02); *A61B 2090/3966* (2016.02)

(58) Field of Classification Search
  CPC .... A61B 2090/3925; A61B 2090/3954; A61B 2090/397; A61B 2090/3908; A61L 31/18; A61N 5/1049; A61N 5/103
  See application file for complete search history.

(56) References Cited

U.S. PATENT DOCUMENTS

| | | | | |
|---|---|---|---|---|
| D715,442 | S * | 10/2014 | Allen | D24/158 |
| 9,615,915 | B2 * | 4/2017 | Lebovic | A61F 2/12 |
| 11,219,502 | B2 * | 1/2022 | Liu | A61B 90/39 |
| 2004/0168692 | A1 * | 9/2004 | Fogarty | A61B 90/39 |
| | | | | 606/116 |
| 2005/0049489 | A1 * | 3/2005 | Foerster | A61B 90/39 |
| | | | | 600/431 |
| 2006/0025795 | A1 * | 2/2006 | Chesbrough | A61B 90/39 |
| | | | | 600/567 |
| 2008/0051868 | A1 * | 2/2008 | Cottone | A61F 2/91 |
| | | | | 623/1.42 |
| 2009/0000629 | A1 | 1/2009 | Hornscheidt et al. | |
| 2011/0066231 | A1 * | 3/2011 | Cartledge | A61F 2/2445 |
| | | | | 623/2.11 |
| 2013/0289389 | A1 * | 10/2013 | Hermann | A61N 5/1015 |
| | | | | 600/424 |
| 2013/0289390 | A1 * | 10/2013 | Hermann | A61N 5/1015 |
| | | | | 600/424 |
| 2017/0333233 | A1 | 11/2017 | Lumauig et al. | |
| 2020/0000477 | A1 * | 1/2020 | Nita | A61B 17/12109 |
| 2020/0397530 | A1 * | 12/2020 | Gleich | A61B 1/00158 |

* cited by examiner a)

b)

c)

12

18

16

14

"Connecting piece" plug connection system a)

3er

22

24

24

24

26

12 b)

2er

26

22

12 c)

4er

22

26

24

12

Fig. 6

Band can be pressed together in length as desired a)

b)

IMPLANTABLE MARKER BODY FOR BREAST TREATMENT

This application is a U.S. national stage application under 35 U.S.C. § 371 (c) of International Application No. PCT/EP2021/052864, filed Feb. 5, 20201, which claims priority to German Patent Application No. 10 2020 000 762.7, filed Feb. 6, 2020, the entire content of each of which is incorporated by reference herein.

The invention relates to an implantable marker body—abbreviated as a marker—for breast therapy, in particular for breast radiotherapy.

A breast radiotherapy marker is used for intraoperative marking of the breast tumor bed for postoperative radiotherapy.

It is required that a breast radiotherapy marker must be resistant to radiation and must not undergo any changes during the radiotherapy. The marker should reliably localize the tumor bed by means of visible marker elements in as precise a manner as possible for subsequent irradiation planning and therapy using integrated radiopaque or x-ray radiation-based imaging, in order to keep the volume of irradiated body tissue as low as possible and protect the surrounding healthy tissue. This also means that the marker must not undergo dislocation.

Dose planning of the radiotherapy can be carried out based on the position of the marker elements of the implanted marker. The farther apart the marker elements are from one another, the more precisely the dose planning can be carried out.

Furthermore, the marker should feel "soft" so that it is not palpable in the breast postoperatively. In addition, the marker must also be usable for MR imaging. The MR image artifacts should be a maximum of 3 times larger than, preferably 1.5 times larger than, or in the optimum case exactly the same size as the marker itself. The MR artifact size is determined by the material, in particular by metal materials, of which the marker elements should preferably consist.

The object of the invention is to provide one or multiple marker body/bodies that meet the aforementioned requirements in the best manner possible.

According to the invention, this object is achieved by means of a marker body (marker) having the features of claim 1. Accordingly, the marker body is composed of a tube or an at least partially tubular body of soft, elastic material that carries multiple radiopaque marker elements. The term "soft elastic" refers to a tube that offers hardly any resistance to an external, deforming force, but returns to its original shape in the absence of external forces.

The at least partially tubular body has two free ends that can be detachably connected to each other. A plug-in connection is preferably provided for this purpose. When the free longitudinal ends of the at least partially tubular body are connected to each other, this gives rise to a ring (also referred to below as a "marker ring" or "tubular ring marker"), which forms the marker body. The elastic forces with which the marker body resists an external force are preferably less than 1N on a 1 mm compression path with an outer ring diameter of 3 cm.

The at least partially tubular body preferably has a lumen at at least one of its free ends into which the other free end of the at least partially tubular body or a connecting element can be inserted in order to connect the two free ends of the at least partially tubular body to each other. The connection is preferably a clamp connection in which at least one of the interconnected free ends of the at least partially tubular body is at least slightly radially enlarged compared to its unconnected state, in order to achieve the clamping action by means of elastic restoring forces. The connection is preferably such that the force required to re-detach the connection is at least 2 N, and particularly preferably at least 20 N.

Preferably, the at least partially tubular body has a continuous lumen or two or more lumens, which together extend over more than half of the total length of the at least partially tubular body. This makes it possible to shorten the at least partially tubular body at the locations where it has a lumen, thus producing a shorter at least partially tubular body, the free ends of which can be plugged together by means of the lumen in order to create a marker body having dimensions adapted to a respective implantation site.

When the at least partially tubular body in its initial state with unconnected ends is straight in a relaxed state, the at least partially tubular body can be formed into an elastic ring by connecting its two free ends to each other, thus giving rise to a ring marker. This marker has an at least approximately circular form when the cross-sections of the at least partially tubular body have the same or similar area moments of inertia and the at least partially tubular body—with the exception of the marker elements—is composed of the same material or materials over its entire length.

This type of tubular ring marker allows multiple point marking for the CT, and at the same time, it can be tailored to the individual patient and adapted (plugged together) to fit any size.

Existing products for this indication require the hospital to have different sizes of the marker in stock depending on the size of the tumor bed. With the tubular ring marker, it is only necessary to have one size in stock, and this size can then be adjusted intraoperatively to the desired length.

The at least partially tubular body is preferably composed of a soft bioresorbable polymer (e.g. PLA, PLLA, polyglycolic acid, polycaprolactone, poly-p-dioxanone, ε-caprolactone, Evonik Resomer, or the like). The polymer is preferably configured such that it is stable in tissue for at least 6 months and is then resorbed. Inside the tube (or clamped to the outside), at intervals of 2 to 3 cm, are radiopaque, preferably metallic marker elements, which are then visible on the CT image. Preferred biocompatible metals for the marker elements are gold, titanium, tantalum or Nitinol. For this purpose, in a lumen of the marker body, small metal cylinders can be used (e.g. approx. 01.5 mm×3 mm). Other geometric shapes are also conceivable, provided that they do not undergo dislocation in or on the at least partially tubular body.

The total length of the at least partially tubular body is preferably between 6 cm, 7.5 cm, 15 cm, 20 cm and 30 cm. At a length of 30 cm, the maximum diameter after the longitudinal ends are inserted into each other is approx. 9.5 cm, which is also sufficient for very large tumor beds post-lumpectomy. The outer diameter of the at least partially tubular body is preferably between 1 mm and 5 mm.

The connection of the free ends of the at least partially tubular body can be carried out either in the configuration of a socket (variant 1), in which the free longitudinal end at which the least partially tubular body was cut is inserted into the other longitudinal end, which has a somewhat expanded diameter. In an alternative variant 2, both longitudinal ends of the at least partially tubular body have the same diameter and are plugged together by means of a connecting element, preferably a connecting pin. This connecting pin is preferably composed of an also bioresorbable plastic that is harder than the material from which the at least partially tubular body is formed. Alternatively, the connecting pin can be made of metal and thus also serve as a marker element that is visible on the CT image. The at least partially tubular body preferably has a lumen at its two longitudinal ends into which the connecting pin can be inserted in order to connect the longitudinal ends of the at least partially tubular body with each other.

In order to prevent migration of the marker body, the marker body is stitched into the tumor bed by means of eyelets (optional) or loops. The at least partially tubular body is flexible and adapts to the shape of the tumor bed. This is done so that the marker body cannot be felt in the breast postoperatively. The flat shape allows adaptation to common oncoplastic surgical techniques.

In an embodiment, in the delivery state, the at least partially tubular body is already present in ring form or in a form that approximates the implantation state. The diameter of the annular preformed at least partially tubular body should preferably be somewhat smaller than the smallest marker body to be formed from the at least partially tubular body, so that the end sections of the at least partially tubular body overlap before the at least partially tubular body is suitably shortened, the longitudinal ends of which are connected longitudinal to each other.

In further variants of the marker body, said body is configured such that multiple at least partially tubular bodies can be connected or are connected to form a marker body.

For this purpose, connecting elements with multiple free ends can be provided, which can be inserted into lumens at the free longitudinal ends of the at least partially tubular body, in order in this manner to allow free longitudinal ends of multiple at least partially tubular bodies to be connected to one another for form a marker body.

According to a further variant, the marker body is formed by two tubular ring markers. For example, two tubular ring markers can be inserted into each other (e.g. rotated by 90°) in order to create a kind of ball. The now three-dimensional shape of the marker would fill or keep open the tumor cavity and prevent the breast from collapsing at this site. The tissue can grow into the marker. In addition to accurate irradiation planning, the marker would support the cosmetic aspect of the reconstruction.

A further embodiment is a modular system, in which a central element—the essentially tubular body—can be connected to itself until the desired length is achieved. The individual essentially tubular bodies can for this purpose be configured to be correspondingly shorter. In this manner, the physician can plug together multiple elements without having to cut anything. Cutting of the product is unnecessary, and in this manner, waste that would have resulted from cutting may be prevented.

According to a further variant, the essentially tubular body has loops at its two longitudinal ends, through which the essentially tubular body itself is guided, resulting in a ring that is adjustable in its width and is thus adaptable to the size of the tumor bed. The continuously adjustable diameter of this marker body can preferably be determined by a clamp mechanism (not shown) on at least one loop (32 or 34) or in steps in which an element of the loop is fixed to the area between the loops by means of mechanical interlocking.

The following is a list of suitable materials for the at least partially tubular body and the connecting elements: chitosan, chitin and derivatives thereof, PGA (polyglycolide/ polyglycolic acid), dextran, PLA (polylactide/polylactic acid), PLLA (poly-L-lactide), PDLA (poly-D/L-lactide), PLDLLA (poly-L-co-D/L-lactide), PLGA (polylactide-co-glycolide), PCL (poly-ε-caprolactone), PEG (polyethylene glycol), PVA (polyvinyl alcohol), PDO (poly-p-dioxanone), PHA (polyhydroxyalkanoate) and PPG (polypropylene glycol)

Moreover, the following non-resorbable materials are also suitable: silicone, PA (polyamide), PPG (polypropylene glycol), Pebax, polyurethane, PE (polyethylene), LDPE and PVDF (polyvinylidene fluoride).

Suitable materials for the marker elements are: gold, platinum, nitinol, tantalum, titanium, plastic with barium sulfate.

A suitable material for resorbable marker elements is magnesium.

Figure 4:
Figure 5:
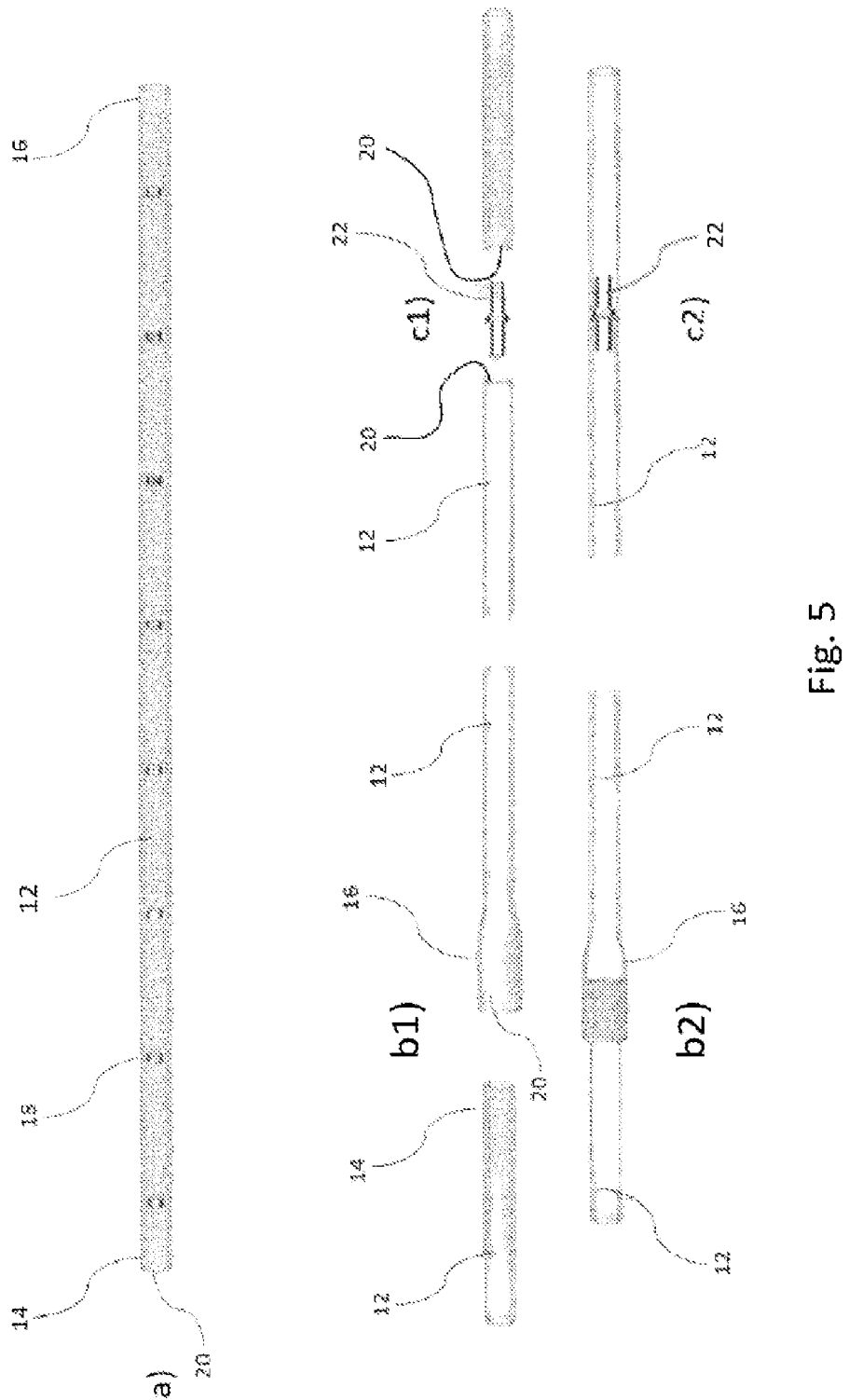
Figure 7:
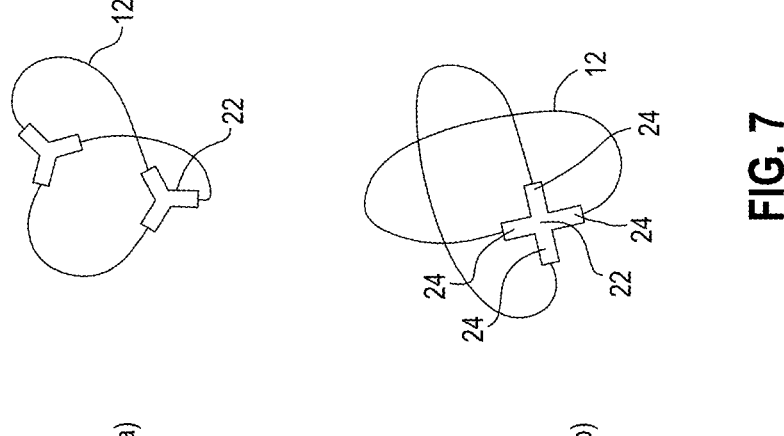
Figure 8:
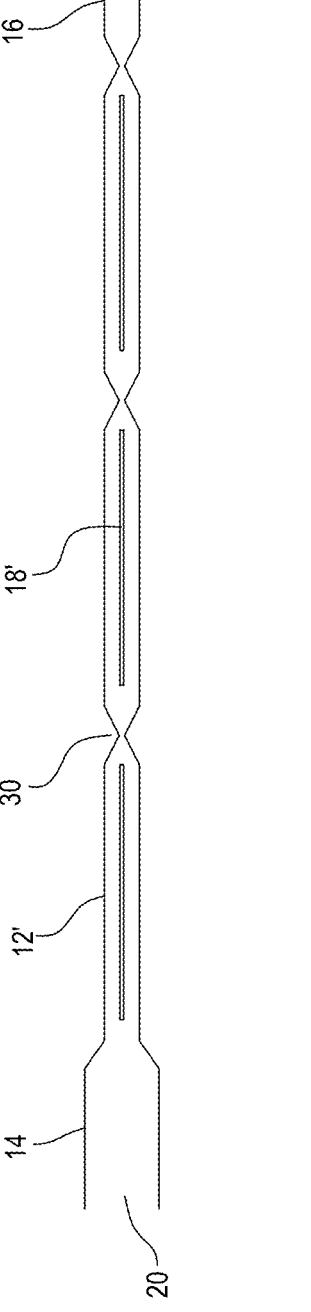
Figure 9:
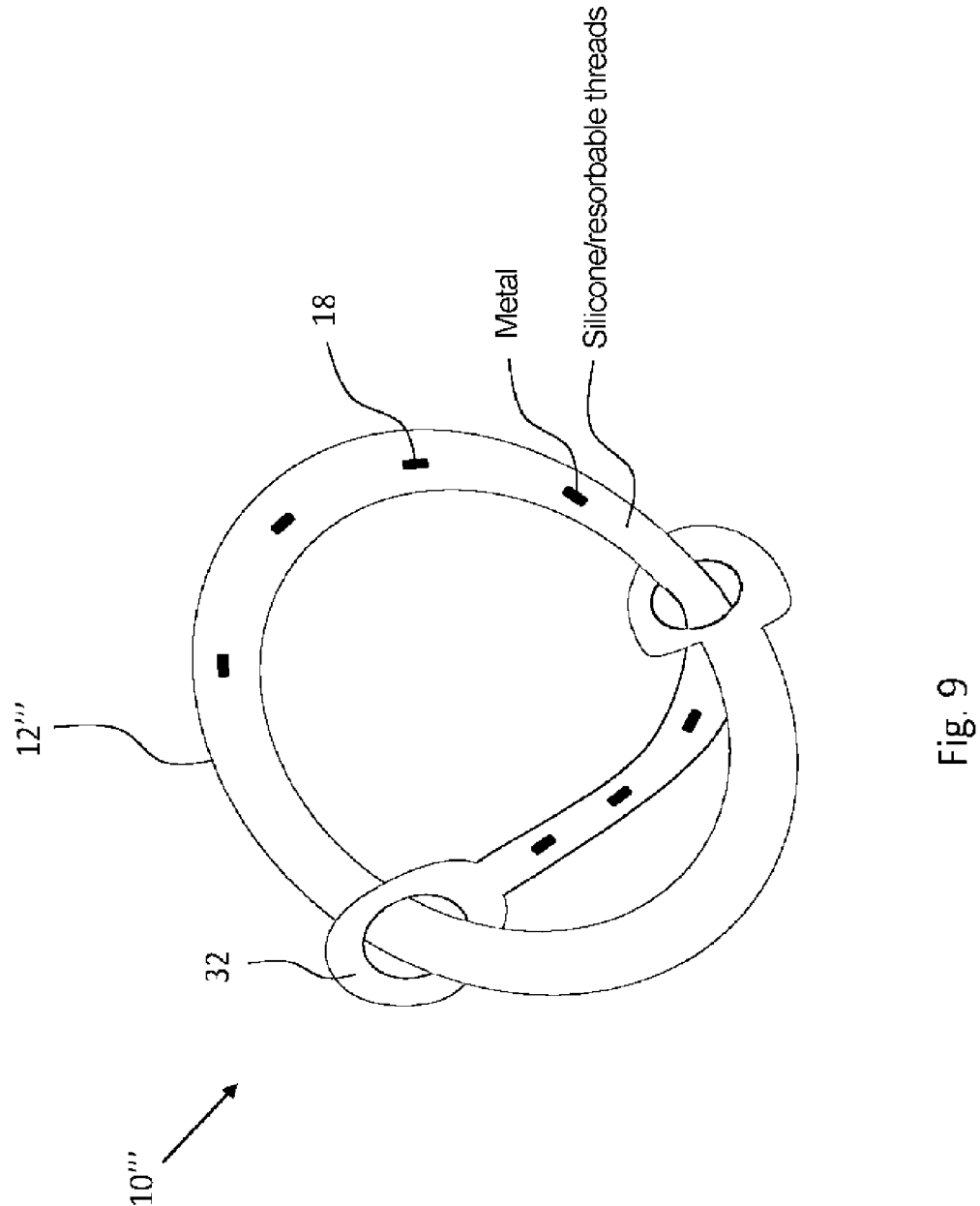
Figure 10:
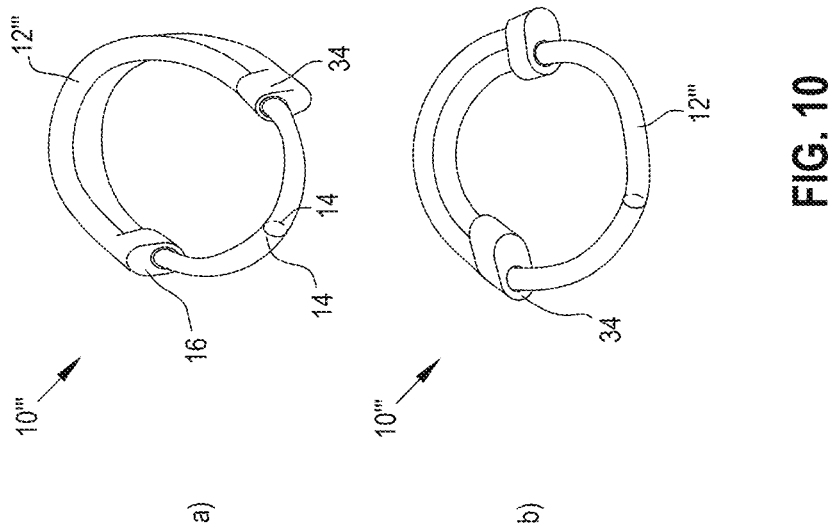
Figure 11:
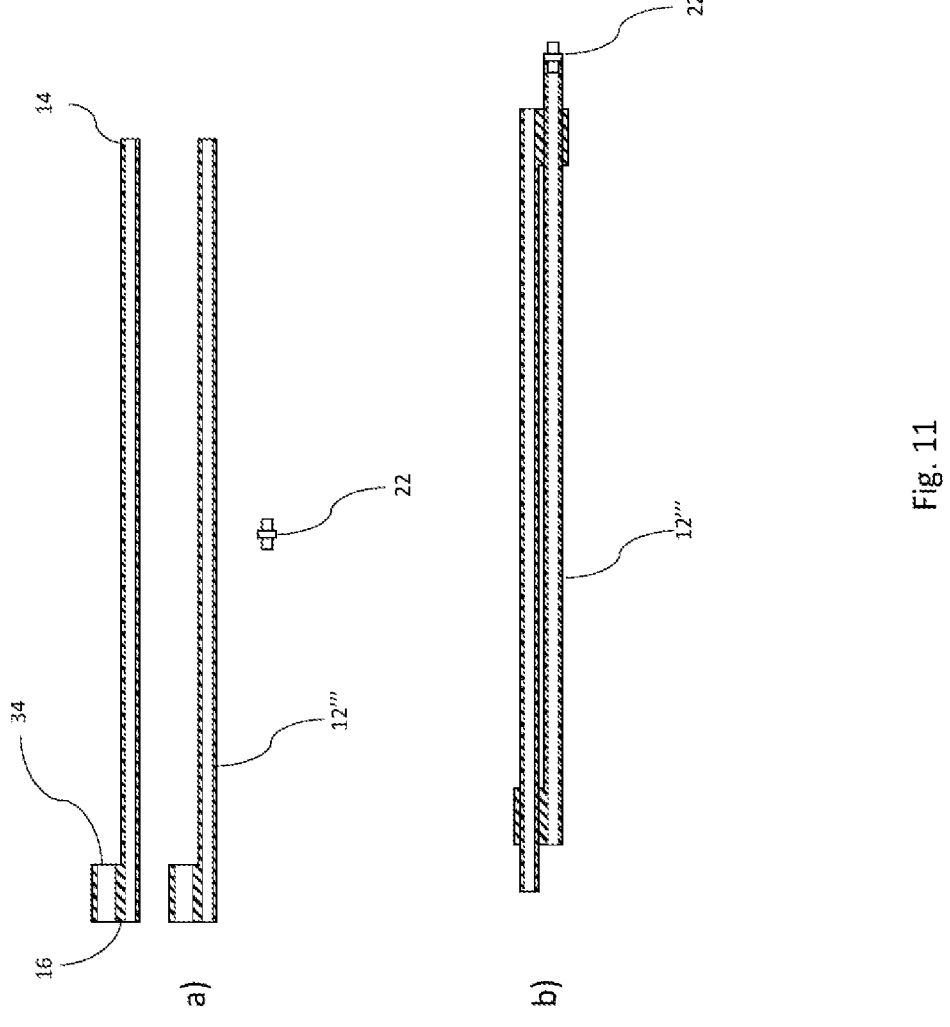
Figure 12:
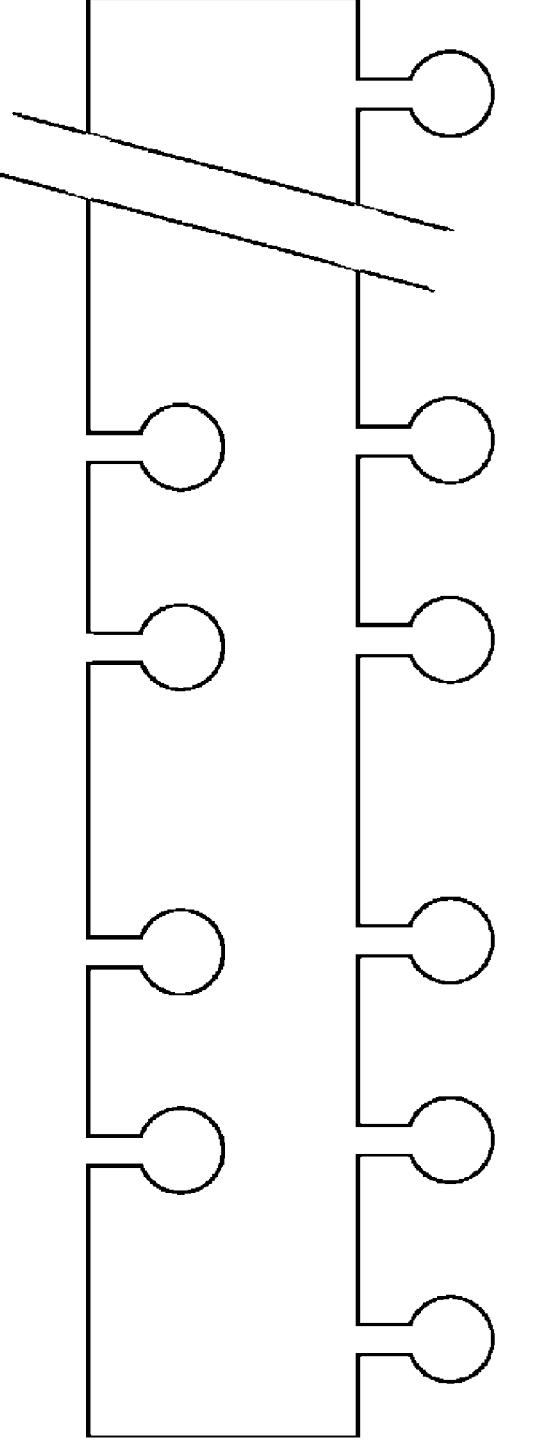
Figure 13:
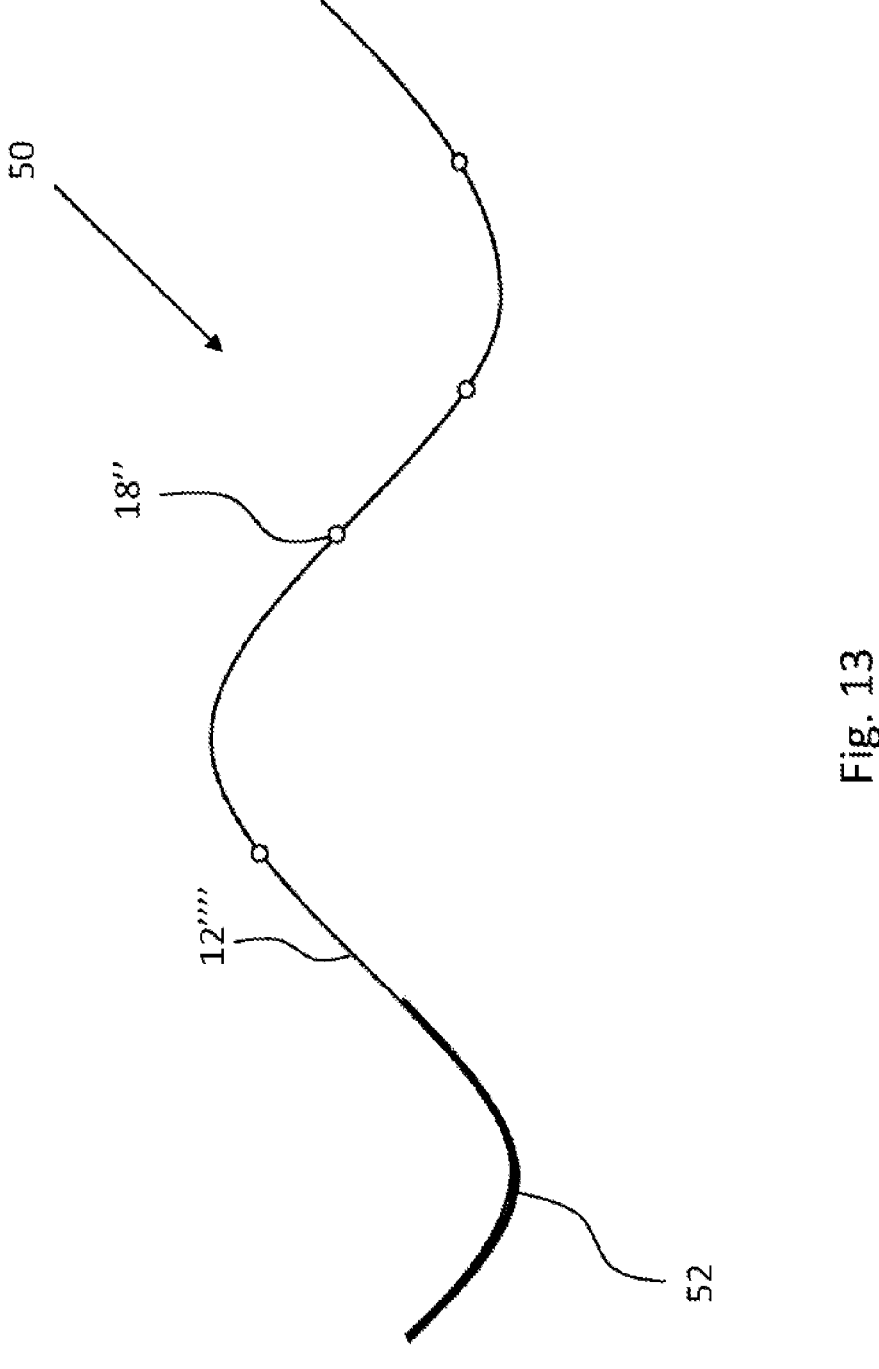
Figure 14:
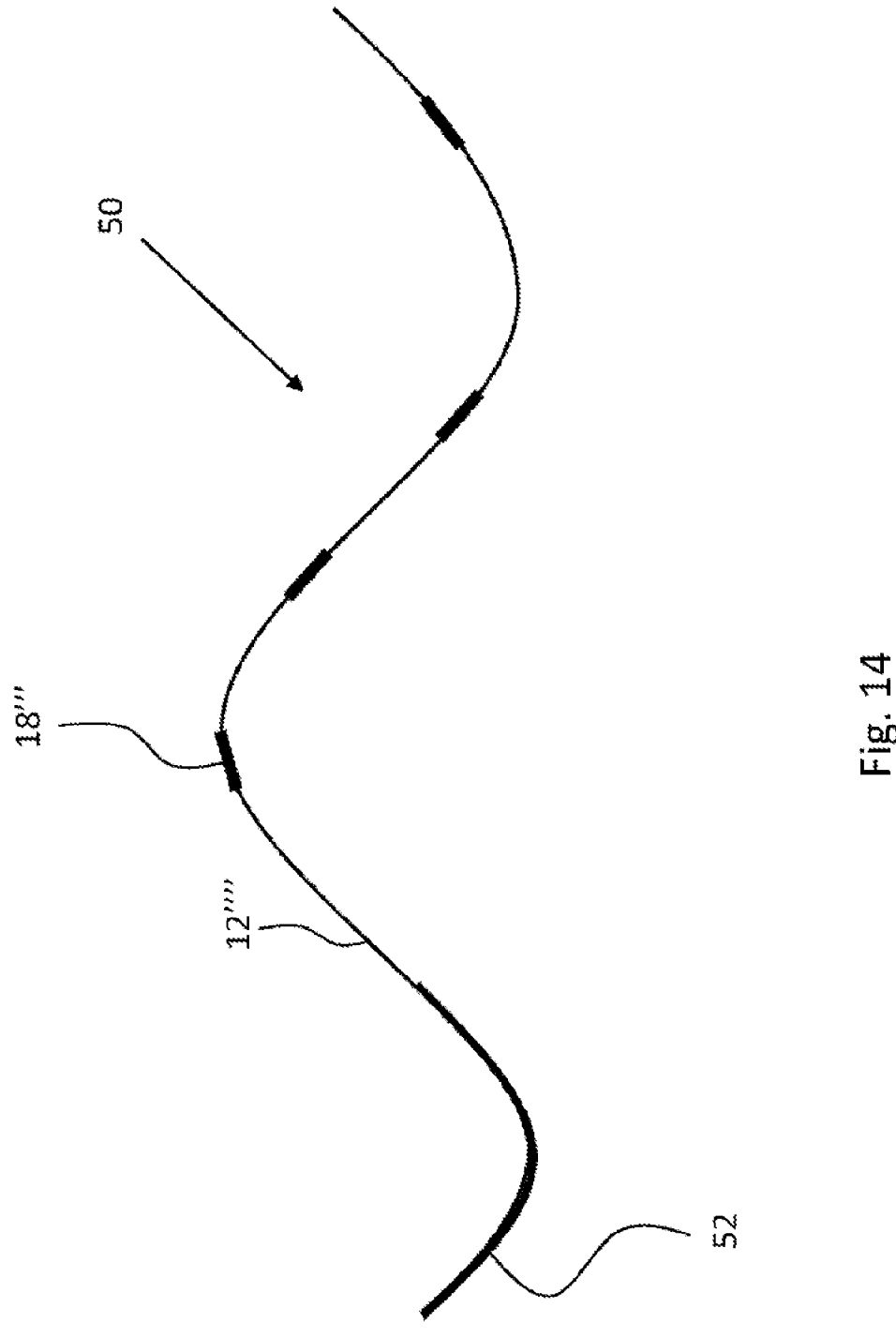
Figure 15:
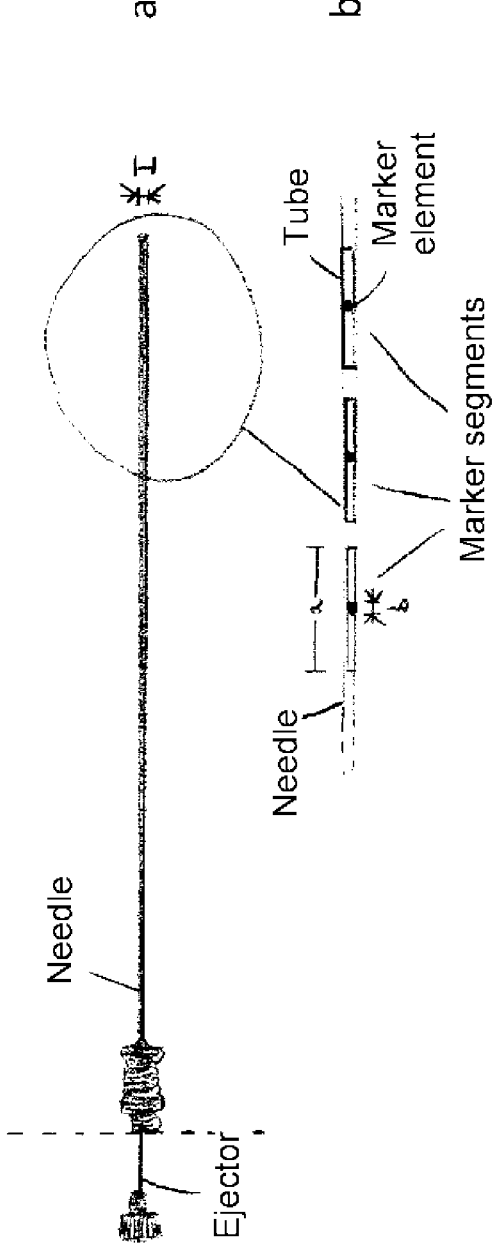
Figure 17:
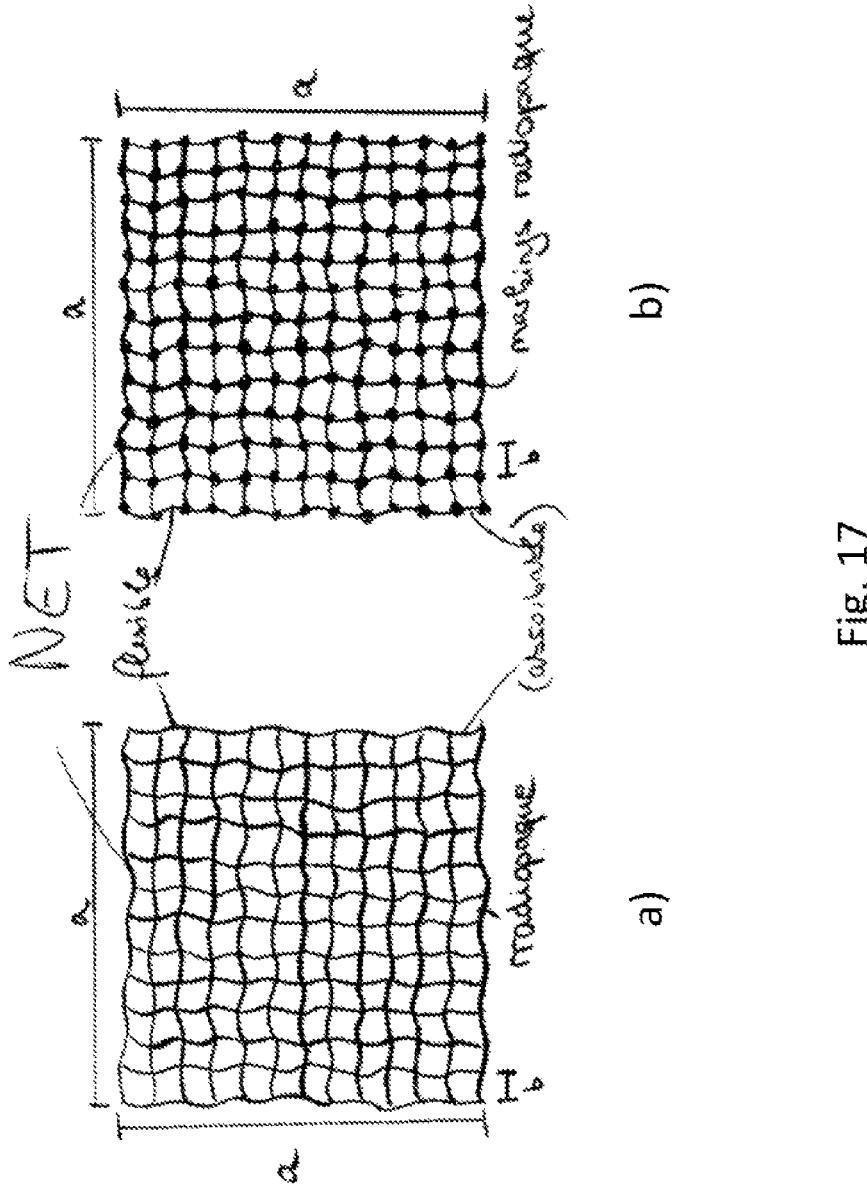
Figure 19:
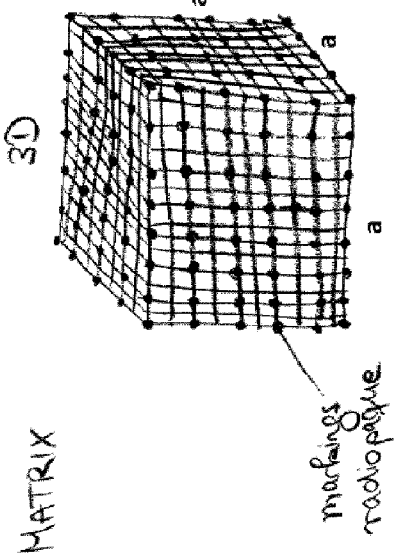
Figure 21:
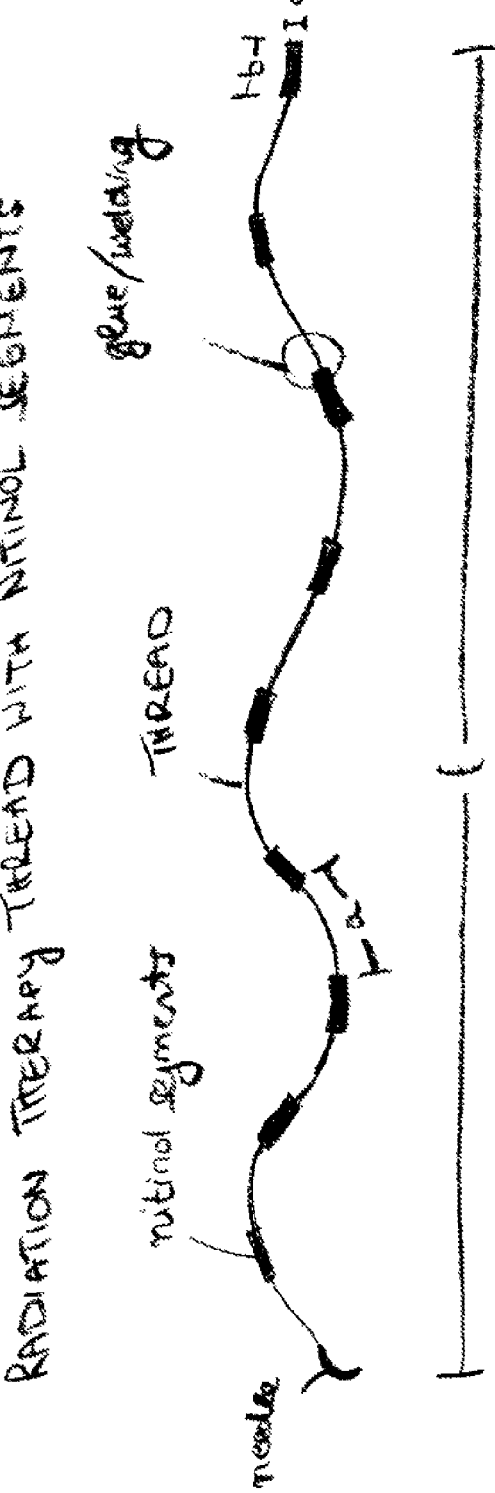

The invention will now be explained in further detail based on working examples with respect to the figures. The figures show the following:

FIG. 1*a*-1*e*: a tubular body (FIG. 1*a*) and a marker body according to the invention composed thereof (FIG. 1*e*) and possible methods for connecting the intraoperatively free longitudinal ends of the tubular body to each other (FIGS. 1*b* and 1*c*) and for intraoperative shortening of the tubular body (FIG. 1*d*);

FIG. 2*a*-2*c*: an alternative variant of a tubular body that can be plugged together to form a marker body according to the invention, wherein the marker body is composed of a plurality of tubular bodies that are plugged together in a longitudinal direction;

FIG. 3*a*-3*c*: FIG. 3*a*, a tubular body and radiopaque marker elements for the tubular body, and in FIGS. 3*b* and 3*c*, detail views of two different variants for connecting the free longitudinal ends of the tubular body;

FIG. 4*a*-4*c*: different marker bodies according to the invention, which are formed by tubular bodies of different lengths;

FIG. 5*a*-5*c*: in FIG. 5*a*, a tubular body, and in FIGS. 5 *b* and *c*, different variants for connecting the longitudinal ends of the tubular body to each other in order to form a marker body according to the invention;

Figure 6:
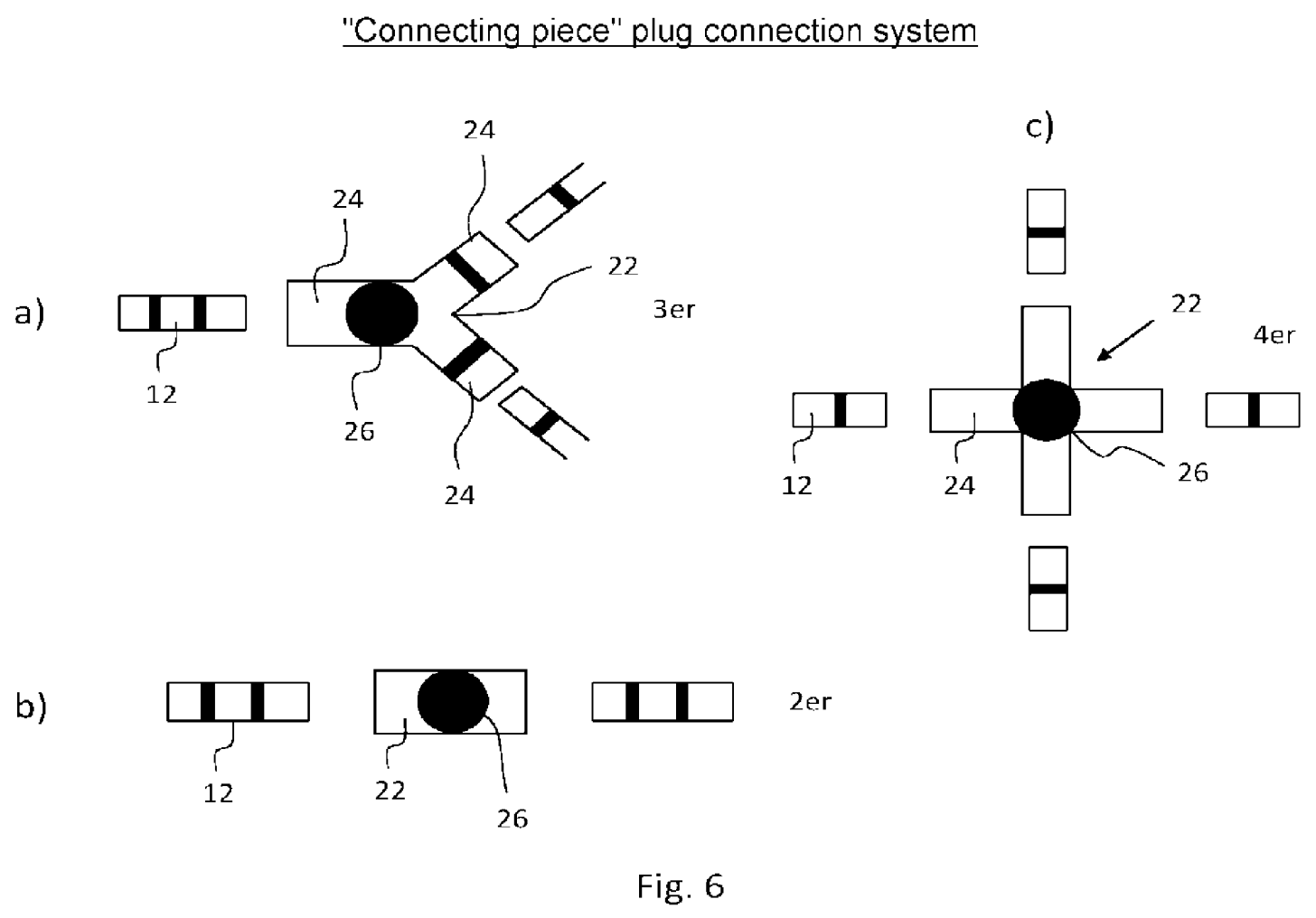

FIG. 6*a*-6*c*: different connecting elements for connecting the free end of one or multiple tubular bodies to a marker body according to the invention;

FIGS. 7*a* and 7*b*: two different variants of a marker body according to the invention, which can be formed with the connecting elements shown in FIG. 6 in conjunction with three or two tubular bodies;

FIG. 8: a variant of a tubular body for a marker body according to the invention with longitudinally extended marker elements and predetermined break points;

FIG. 9: a variant of a marker body according to the invention, which is adjustable in width by means of eyelets on its two longitudinal ends and is therefore adaptable to an implantation site;

FIGS. 10*a* and 10*b*: two variants of a marker body according to FIG. 9 with differing orientations and configurations of the eyelets designed as sleeves at the longitudinal ends of the tubular body;

FIGS. 11*a* and 11 *b*: in FIG. 11*a*, two tubular bodies and one connecting element, which can be put together to form the marker bodies according to FIG. 10, and FIG. 11 *b* illustrates how two tubular bodies according to FIG. 11*a* are first pushed together and then plugged together at their longitudinal ends with the connecting element to form a closed marker body;

FIG. 12: a variant of a body for a marker body with connecting elements, which can be connected to each other in a puzzle-like manner;

FIG. 13: a first variant of a marker body with a longitudinal end configured as a curved needle;

FIG. 14: a second variant of a marker body with a longitudinal end configured as a curved needle;

FIGS. 15*a* and 15*b*: an alternative product concept with a plurality of marker elements that are held in a needle;

FIGS. 16*a* and 16*b*: further views of the product concept of FIG. 15;

FIGS. 17*a* and 17*b*: an alternative product concept in the form of a flexible mesh;

FIGS. 18*a* and 18*b*: an alternative product concept in the form of a compressible ball;

FIG. 19: an alternative product concept in the form of a 3D matrix;

FIGS. 20*a* and 20*b*: an alternative product concept in the form of resorbable magnesium spheres connected to a resorbable wire or magnesium wire;

FIG. 21: an alternative product concept in the form of a radiotherapy wire with metal segments; and FIG. 22*a*-22*d*: alternative product concepts in the form of a silicone marker or a hydrogel marker.

A marker body according to the invention 10 (see FIG. 1*e* and FIGS. 4*a*-*c*) is composed according to a first variant of a tubular body 12, the free longitudinal ends 14 and 16 of which are connected to each other in such a way that the marker body 10 at least approximately has the shape of a circular ring hat. The tubular body 12 carries a plurality of marker elements 18, which can be applied to the tubular body 12 or inserted into the tubular body 12; see FIGS. 1-5.

The tubular body 12 can be configured as a tube with a continuous lumen or can have lumens in sections—in other words, no continuous lumen.

As shown in particular in FIG. 1*d*, the tubular body 12 can be shortened in order in this manner to allow production of marker bodies 10 with different diameters, as shown in FIGS. 4*a*-*c*.

Preferably, the tubular body 12 is shortened where it has a lumen. The respective lumen 20 of the tubular body 12 serves to connect the longitudinal ends 14, 16 of the tubular bodies 12 with each other. According to a first variant (see FIGS. 1*b*, 3*b*, 4*a*-*c* and 5*b*), one of the longitudinal ends 14 or 16 of the tubular body 12 is widened so that the respective other longitudinal end 16 or 14 can be plugged into the correspondingly widened longitudinal end in order in this manner to connect the two longitudinal ends 14, 16 of the tubular bodies 12 with each other and produce the marker body according to the invention 10.

Figure 3:
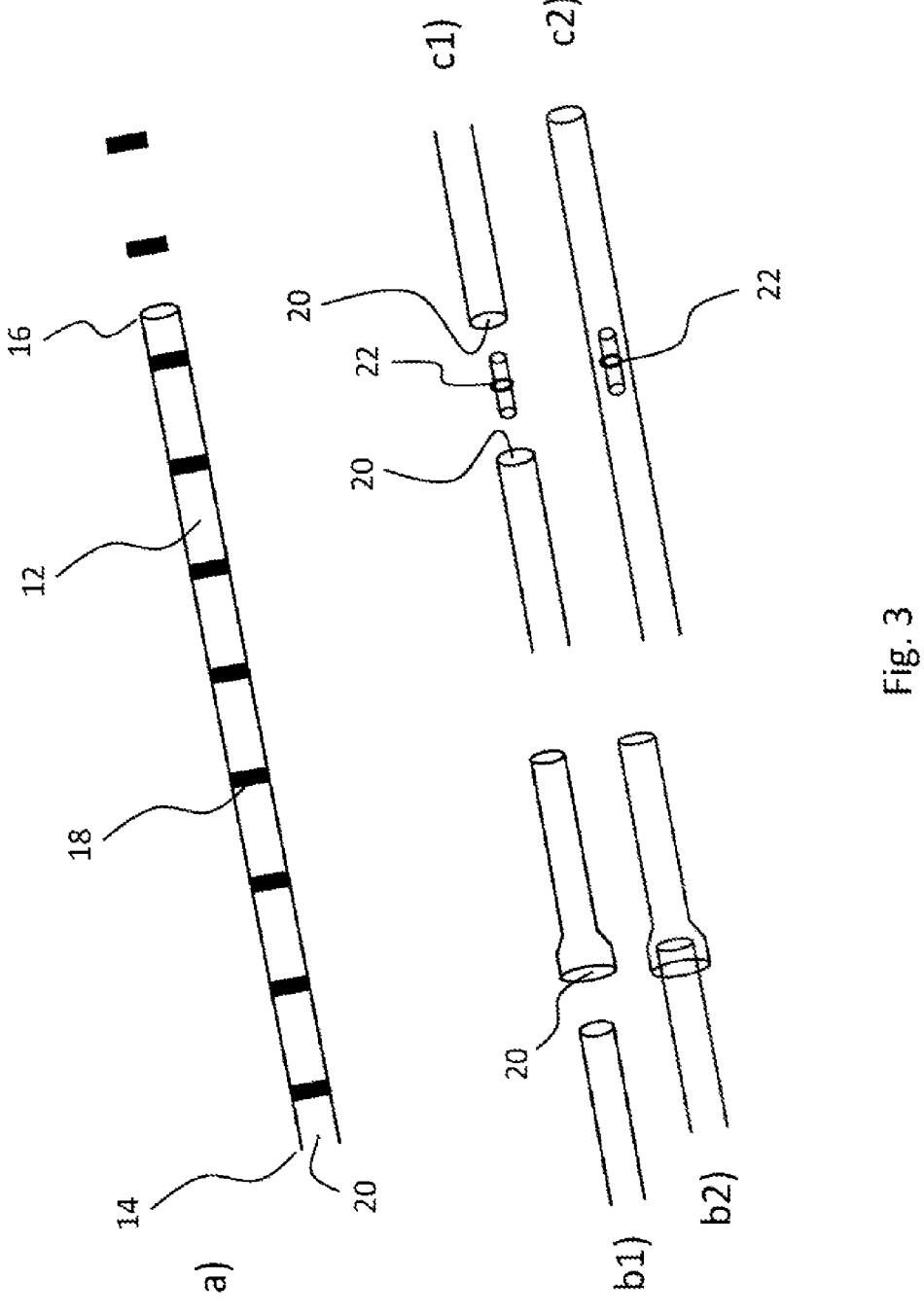

Alternatively, the lumens 20 at the two longitudinal ends 14 and 16 of the tubular body 12 can also have the same inner diameter. In this case, a separate connecting element 22—for example a connecting pin—can be provided, which can be plugged into the lumens 20 at the two longitudinal ends 14 and 16 of the tubular body 12 in order to allow these longitudinal ends 14 and 16 of the tubular body to be connected to each other; see for example FIGS. 1*c*, 3, and 5*c*. The connecting elements 22 can be configured as connecting pins as shown in FIGS. 1*c*, 3*c* and 5*c*. Alternatively, however, the connecting elements 22 can themselves have more than two connecting ends 24, for example three connecting ends 24 (see FIG. 6*a*) or four connecting ends 24 (see FIG. 6*c*). Each of the connecting ends 24 can either be configured as sleeves into which the free longitudinal ends 14 or 16 of a tubular body 12 can be plugged, or the free connecting ends 24 can be configured as rods that can be plugged into the respective lumens 20 at the free longitudinal ends 14 or 16 of the tubular body 12.

Each of the connecting elements 22 can also have at least one marker element 26. Alternatively, the connecting elements themselves may also be configured to be radiopaque so that no separate marker element 26 is required.

With the connecting elements 22 having more than two connecting ends 24 shown in FIG. 6*a* or in FIG. 6*c*, marker bodies can be produced such as those shown schematically in FIGS. 7*a* and 7*b*. For example, a marker body composed of two connecting elements 22 with three connecting ends 24 and three tubular bodies 12 each can be plugged together, as shown in FIG. 7*a*. In order to allow adjustment of the size of such a marker body 10' at the respective implantation site, tubular bodies 12 can be correspondingly shortened in this case as well.

With a connecting element 22 having four connecting ends 24 in conjunction with two tubular bodies 12, a marker body 10" can be plugged together having for example the shape shown schematically in FIG. 7*b*. In this case as well, the respective tubular body 12 can be correspondingly shortened in order to adjust the marker body 10" at the respective implantation site. Not shown is a modification of the marker body 10" of FIG. 7*b* in which, similarly to the example shown in FIG. 7*a*, two connecting elements 22 with four connecting ends 24 each are provided.

For example, in the marker elements 18 shown in FIGS. 7*a* and 7*b*, even when no marker elements 18 are shown, the tubular bodies 12 have such marker elements. In fact, the tubular bodies 12 in the marker bodies 10' and 10" according to FIGS. 7*a* and 7*b* can have the same appearance as the tubular body 12 shown in FIGS. 1*a*, 3*a* and 5*a*.

The tubular bodies 12 are preferably made from a bioresorbable plastic. The bioresorbable materials listed in the following are suitable: chitosan, chitin and derivatives thereof, PGA (polyglycolide/polyglycolic acid), dextran, PLA (polylactide/polylactic acid), PLLA (poly-L-lactide), PDLA (poly-D/L-lactide), PLDLLA (poly-L-co-D/L-lactide), PLGA (polylactide-co-glycolide), PCL (poly-ε-caprolactone), PEG (polyethylene glycol), PVA (polyvinyl alcohol), PDO (poly-p-dioxanone), PHA (polyhydroxyalkanoate) and PPG (polypropylene glycol).

Moreover, the following non-resorbable materials are also suitable: silicone, PA (polyamide), PPG (polypropylene glycol), Pebax, polyurethane, PE (polyethylene), LDPE and PVDF (polyvinylidene fluoride).

The marker elements 18 are preferably composed of a radiopaque metal, such as gold, platinum, nitinol, tantalum, titanium, or plastic with barium sulfate.

A suitable material for resorbable marker elements 18 is magnesium.

The marker elements 18 can be clamped onto the outside of the at least partially tubular body. Alternatively, the marker elements 18 can be inserted into corresponding lumens 20 of the tubular body 12 or be cast into the carrier material of the tubular body 12, for example by molding the carrier material around the marker elements, for example in the injection molding process.

A marker body 10 can also be composed of multiple tubular bodies 12 that are connected to each other at their longitudinal ends. According to a variant, it is provided that the tubular bodies are relatively short, so that do not need to be shortened for adjustment to an implantation site; rather, multiple tubular bodies 12 can be plugged together to form one marker body 10. Examples of this are shown in FIGS. 2*b* and 2*c*. FIG. 2*b* shows a tubular body 12 composed of multiple tubular bodies 12, as shown for example in FIG. 2*c*.

Figure 2:
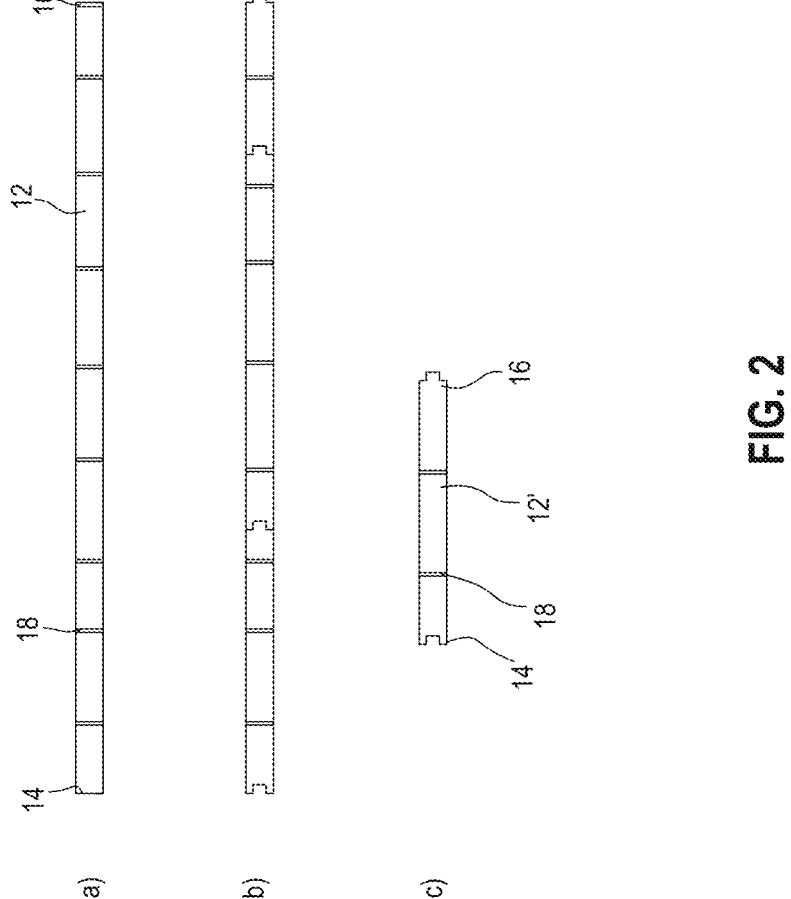

As can also be seen from FIG. 2, the tubular bodies 12 can also have only a short lumen 20 at one longitudinal end 14, and at the other longitudinal end 16, a corresponding pin-like projection 28 that can be plugged into the lumen 20 in order to produce a connection between the longitudinal ends 14 and 16 of the tubular body 12. In this case, no separate connecting element is required, nor is it necessary to provide a widened longitudinal end. It is understood that short tubular bodies 12 as shown in FIG. 2c can also have longitudinal ends 14 and 16, as shown for example in FIGS. 1b, 1c, 3b, 3c, 5b and 5c. Accordingly, the marker body according to FIG. 2 can also be provided with connecting elements 22 for connecting the longitudinal ends 14 and 16, or one of the longitudinal ends 14 or 16 can be widened, as shown for example in FIG. 1b, 3b or 5b.

In order to shorten a tubular body 12' to a desired length even without a tool, the body may have predetermined break points 30, as shown in the example of FIG. 8. The tubular body 12' shown in FIG. 8, by plugging together of its free longitudinal ends 14 and 16, can be formed into a marker body 10 in the same manner as the tubular body 12 shown in FIGS. 1-5. For this purpose, a longitudinal end 14 is correspondingly widened so that the other longitudinal end 16 can be plugged into the widened longitudinal end 14.

With respect to the marker elements 18, FIG. 8 shows that instead of having he shape of relatively short metal rings, these may also be configured as somewhat longer metal rings formed from somewhat longer metal rods 18' that are inserted into corresponding lumens of the tubular body 12' or are cast into the carrier material of the tubular body 12'. In this case as well, the carrier material of the tubular body 12' is preferably a bioresorbable plastic.

In order to allow virtually continuous adaptation of a marker body 10''' to the respective implantation site, a tubular body 12''' can also be provided that has a loop 32 (FIG. 9) or a sleeve 34 at one longitudinal end or at two longitudinal ends (FIGS. 10a, 10b, 11a and 11b) through which the tubular body 12''' can be fed, in order in this manner to obtain a displaceable connection between the respective longitudinal end of the tubular body 12''' and the remaining tube body 12'''. Marker bodies 10''', as shown for example in FIGS. 10a and b, can be composed of two tubular bodies 12''' and one connecting element 22. This is shown in FIGS. 11a and 11b. FIG. 11a shows two tubular bodies 12''' and a connecting element 22. FIG. 11b shows how the tubular bodies 12''' can first be plugged together in such a manner that they can slide into the sleeves 34 at their respective longitudinal end 16. The other longitudinal ends 14 of the tubular body 12''' respectively can then be connected to each other using the connecting element 22 in such a manner that an annular marker body 10''' that is adjustable in width is produced, as shown in FIG. 10a or 10b. The continuously adjustable diameter of this marker body 10''' can preferably be fixed by means of a clamping mechanism, not shown, on at least one loop 32 or sleeve 34 or in steps in which an element is fixed to the area between the loops by means of mechanical interlocking.

Marking elements 18 that are provided in the embodiments according to FIGS. 9 to 11 in the same manner as in the embodiments according to FIGS. 1 to 5 are not shown in all of the figures for the purpose of simplification.

FIG. 12 in turn shows a further variant, wherein instead of a tubular body, a body is provided that has projections 40 and corresponding recesses 42 that can be connected to one another like the pieces of a puzzle in order to produce a marker body that has a desired diameter. Marking elements 18 that are provided in the embodiments according to FIG. 12 in the same manner as in the embodiments according to FIGS. 1 to 5 are not shown in FIG. 12 for the purpose of simplification.

FIGS. 13 and 14 show that instead of marker bodies 10 that are composed of tubular bodies 12, thread-like marker bodies 50 can also be provided that are configured at one longitudinal end in the manner of a curved metal needle 52.

It can also be seen from FIGS. 13 and 14 that the marker elements 18 can be provided with different shapes. The marker elements 18''' in FIG. 13 are spherical and fixed on the outside of the thread-shaped body 12''''. The marker elements 18'''' in FIG. 14 are spindle-shaped and also fixed on the outside of the thread-shaped body 12''''.

10, 10', 10''' 10 Marker bodies
12, 12', 12''' Tube-like bodies
14, 16 Free longitudinal ends of the tubular body
18 Marker elements
18' Metal rods as marker elements
20 Lumen
22 Connecting element
24 Connecting ends
26 Marker element
28 Projection
30 Predetermined break points
32 Loop
34 Sleeve
40 Projection
42 Recess
50 Marker body
52 Metal needle Further alternative product concepts are explained in the following.

Figure 16:
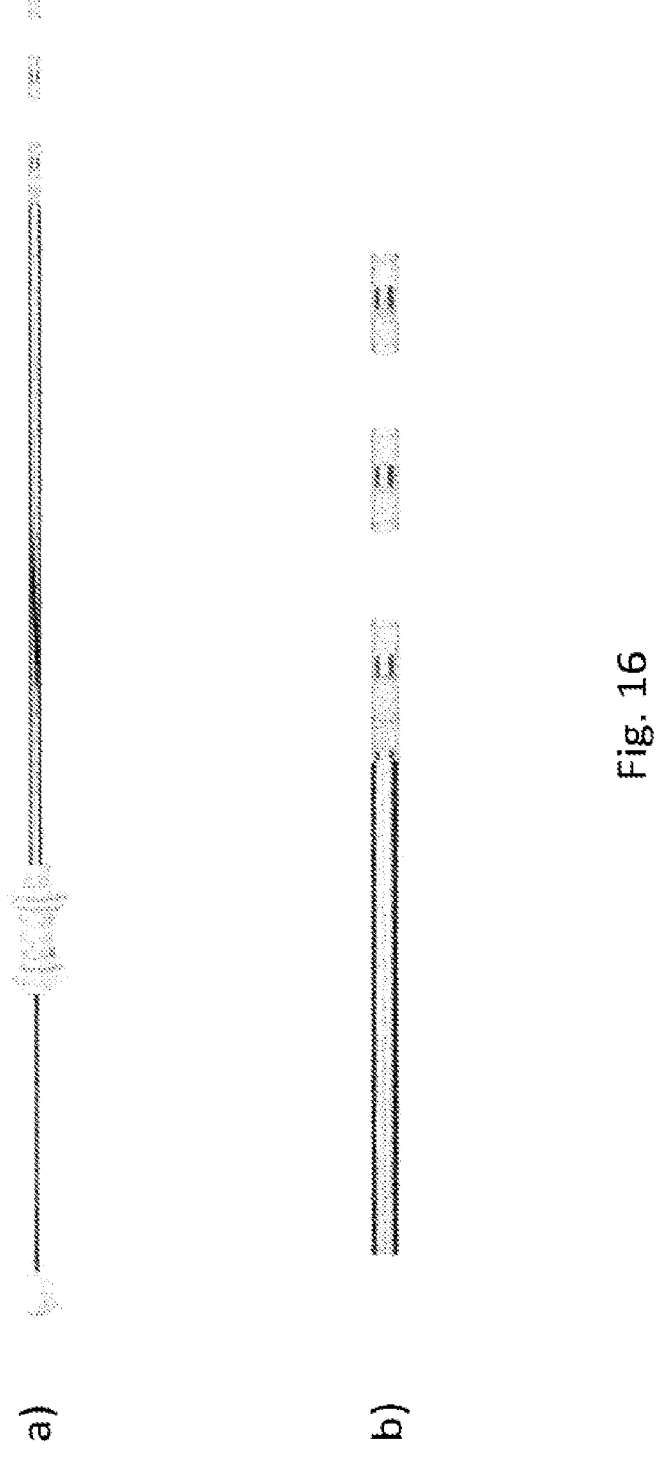

FIG. 15 and 16: Drawing of the product concept: Multiple marker elements in a needle for ejection into the tumor bed Description of the Product Concept:

The concept comprises multiple marker segments (e.g. 3, 5 or up to 10), a needle (in which the segments are pre-loaded) and an ejector with which the marker segments are individually ejected from the needle.

Each marker segment is composed of a tube and a marker element that is cast into the tube.

All of the marker segments are pre-loaded in a needle—one after the other—and can be individually ejected from the needle with an ejector. The needle has an inner diameter I of e.g. 1-3 mm. Each marker segment has a length a of e.g. 2-20 mm, and accordingly, the needle is also several cm long so that all of the marker segments can be housed in said needle.

The tube is composed of a soft bioresorbable polymer (e.g. PLA, PLLA, polyglycolic acid, polycaprolactone, poly-p-dioxanone, ε-caprolactone, Evonik Resomer, or the like). The polymer should be configured such that it is stable in the tissue for approx. 6 months and is then resorbed, or it can be configured to remain in the tissue permanently. The tube has a smaller diameter than the inner diameter of the needle. The tube can be made of a material that increases its volume on contact with water (e.g. a hydrogel). The tube can also be coated in order to ensure biocompatibility, for example. Or the tube can be coated in order to ensure that it is pushed out of the cannula.

Inside the tube, e.g. in the middle of each segment, is a marker element. The marker elements are characterized by being visible on x-rays and CT images. Biocompatible metals such as gold, titanium or Nitinol are conceivable for this purpose. Materials such as magnesium, carbon and calcium, which absorb x-ray radiation, are also conceivable.

The marker elements can for example take on the shape of small spheres (outer diameter b 0.5-3 mm) or cylinders (outer diameter 0.5-3 mm, length 0.5-3 mm). Other geometric shapes, such as cubes, tetragons, hexagons, and octagons are also conceivable.

During application, a segment is pushed out of the needle at particular site and placed. After this, the needle can be guided to another site, and a further segment can be placed there. Thus a single needle can be used to distribute the segments throughout the entire tumor bed.

Drawing of the Product Concept:

FIG. 17

Product concept: Flexible mesh

Description of the Product Concept:

The flexible mesh can be adapted to the shape of the wound cavity and is fastened to the margins of the wound cavity using resorbable suture material or tissue adhesives (such as fibrin adhesives). This ensures that the mesh does not migrate and the margins of the tumor beds are permanently identifiable.

The mesh should not be palpable in the breast postoperatively. It is composed of a polymer or copolymer (for example glycolide and trimethylene carbonate, polyglycolic acid-caprolactone). The polymer should be configured such that it is stable in the tissue for approx. 6 months and is then resorbed. A non-resorbable mesh would also be conceivable (i.e. of polypropylene, polyester or polyamide). If non-resorbable material is used, flexibility must be constructively achieved in order to obtain the desired non-palpability. The mesh is available in different sizes (depending on the size of the tumor bed, margin length a=5, 10, 15, 20 and 25 cm) or can be cut to the desired size, so that it is individually adaptable to various tumor beds and different sizes. The distance b between the meshes is 0.5 to 4.0 mm. The flat shape allows adaptation to common oncoplastic surgical techniques.

One possibility would be for the mesh per se to be radiopaque (addition of a radiopaque material such as BaSO₄, tantalum, gold, titanium) and thus clearly visible on CT. Based on CT images, exact irradiation of the tumor bed can be planned, thus protecting the surrounding health tissue from irradiation. Another possibility would be to equip the visible mesh with radiopaque markers (markers of titanium, platinum, tantalum, gold at intervals b of approx. 0.5-4.0 mm, or up to a multiple of these values by omitting several nodes) and to use the multiple point markers as a reference for the irradiation planning. Because the mesh can be adapted to the shape of the tumor beds, this makes 3D orientation possible in irradiation planning.

Figure 18:
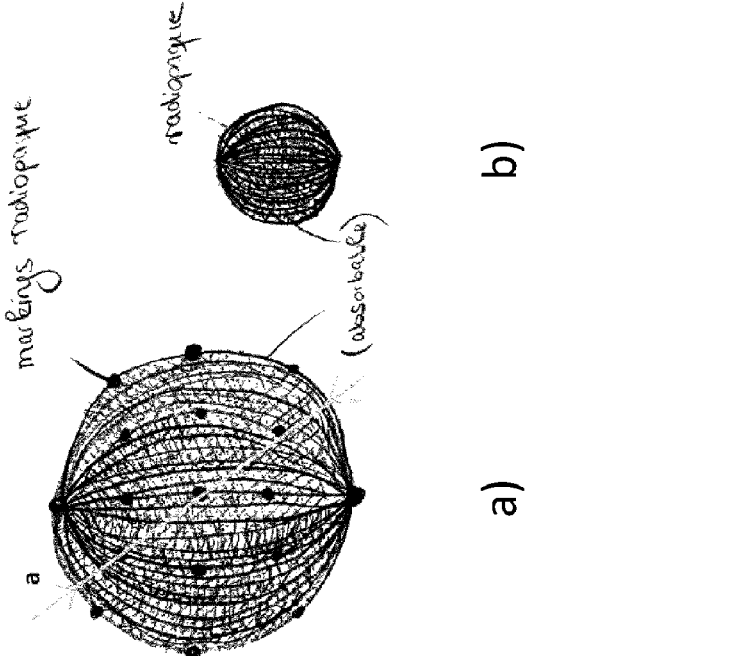

FIGS. 18 and 19: Drawing of the product concept

Product concept: 3D matrix/compressible ball

Description of the Product Concept:

The compressible and postoperatively non-palpable 3D matrix/compressible and postoperatively non-palpable ball (referred to in the following as the marker) constitutes a (porous) resorbable scaffolding and is composed of a polymer (e.g. polydioxanone, collagens or polyethylene glycol), which after implantation is to allow regeneration of the natural breast tissue. The polymer is to be configured such that it is stable for approx. 6 months in the tissue and is then resorbed. In addition, the resorption rate is matched to the growing tissue. If non-resorbable material (such as silicone) is used, flexibility must be constructively achieved in order to obtain the desired non-palpability. The marker could be produced by a 3D printing method.

The marker is available in different sizes (depending on the size of the tumor bed, margin length/diameter a=1, 2, 3, 4 and 5 cm) or can be cut/torn to the desired size in the OP (at predetermined break points). In order to prevent the marker from migrating, it is fastened to the margin of the tumor bed.

One possibility would be for the marker per se to be radiopaque (addition of a radiopaque material such as BaSO₄, tantalum, gold, titanium) and thus clearly visible on CT. Another possibility would be to equip the marker with radiopaque markers arranged at certain intervals inside and on the edge of the matrix/ball (markers of platinum, tantalum, gold at intervals of approx. 0.51 cm). The multipoint markers thus provide a 3D orientation in space and serve as a reference for the irradiation planning. Based on CT images, exact irradiation of the tumor bed can be planned, thus protecting the surrounding healthy tissue from irradiation.

The marker also fills the three-dimensional shape of the tumor cavity, thus preventing the breast from collapsing at this site. The tissue can grow into the marker. In addition to accurate irradiation planning, the marker would support the cosmetic aspect of reconstruction.

Figure 20:
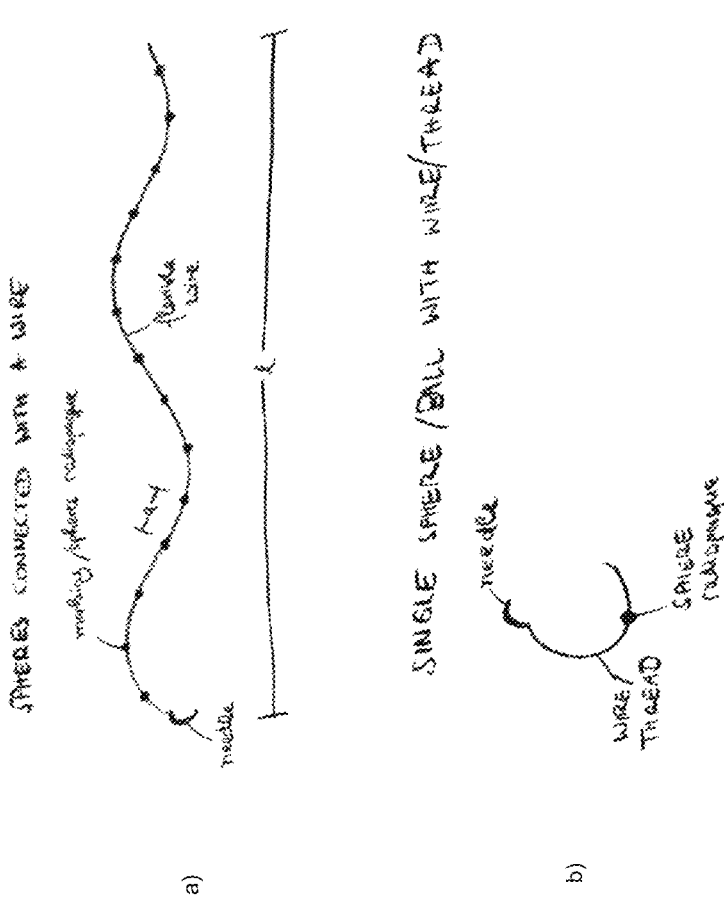

FIG. 20: Drawing of the product concept:

Product concept: Resorbable magnesium spheres (as x-ray markers) connected to a resorbable thread/wire Description of the Product Concept:

The resorbable magnesium spheres (as x-ray markers) (the spheres need not be composed of pure magnesium, but can also be composed of a magnesium alloy, such as e.g. magnesium and neodymium as an additive, which makes it stronger and highly moldable) are connected to one another with a resorbable thread/wire (for example of magnesium/magnesium alloy or polylactic acid). The thread/wire is plastically deformable and thus adaptable to the wound cavity. The thread/wire can be cut to the desired size/length (total length I of the thread/wire=30-50 cm, interval a of the x-ray markers=1-3 cm). A needle is attached to the front end of the thread/wire so that the thread/wire, including the magnesium spheres, can be directly stitched into the wound cavity. This gives rise to a three-dimensional construct, which allows the wound cavity to be reliably localized and based on which the irradiation planning can be carried out.

The resorption time of the magnesium spheres can be controlled by means of various coatings. The coating is to be configured such that the magnesium spheres are stable for approx. 6 months in the tissue and are then resorbed. As a variant, if magnesium is not sufficiently radiopaque, materials such as tantalum or gold can also be used as x-ray markers.

Drawing of the Product Concept:

FIG. 21

Product Concept:

Radiotherapy Thread with Metal Segments

Description of the Product Concept:

The product concept has the shape of a thread into which a plurality of marker elements is incorporated. The thread is made of a material used for surgical thread. The thread is composed of a material that is resorbed after a period of time (e.g. PLA, i.e. polylactic acid). The thread is (plastically) deformable and thus adaptable to the wound cavity. The thread can have a length I of for example 30-100 cm. The diameter of the thread roughly corresponds to the diameter of the other suture material.

The marker elements are characterized by being visible on x-ray and CT images. The marker elements are also characterized in that they are similar to the thread in flexibility, and in the ideal case, even have the same diameter. Conceivable for this purpose are threads, strands or thin wires of biocompatible metals such as e.g. gold, titanium or metal alloys such as e.g. Nitinol.

Each marker element can for example have a length b of 5-20 mm. For example, 5-50 such elements can be distributed along the entire length of the thread. The marker elements can be uniformly distributed along the thread, or rather unevenly distributed.

In order to be able to produce the radiotherapy threads, for example, the marker elements are connected to thread segments by adhesive bonding, welding, lasers, etc. The marker elements can also be cast or pressed into the thread.

A needle is attached to the front end so that the radiotherapy threads, including the Nitinol segments, can be directly stitched into the wound cavity. This gives rise to a three-dimensional construct, which allows the wound cavity to be reliably localized and based on which the irradiation planning can be carried out.

Figure 22:
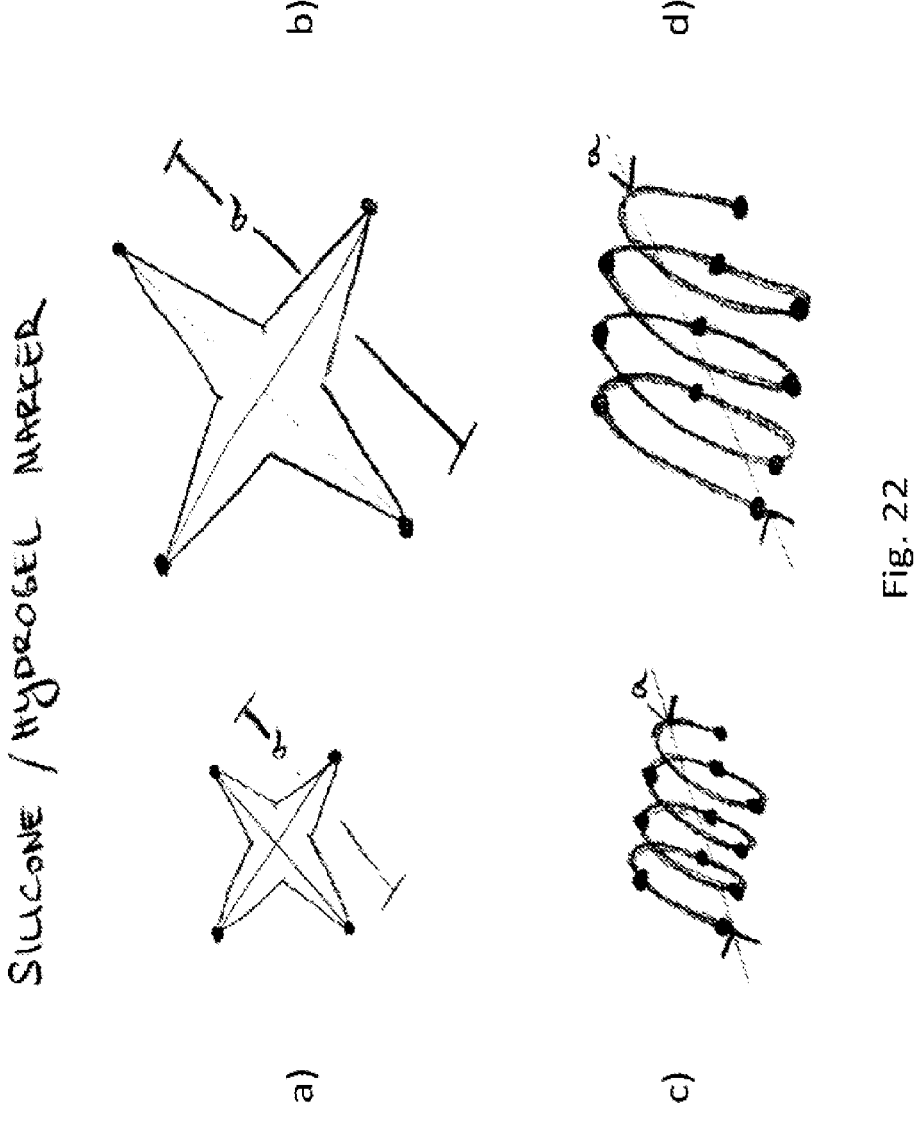

Drawing of the product concept: FIG. 22

Product concept: Silicone marker/hydrogel marker

Description of the Product Concept:

a.) Silicone as a Basic Material:

(available as silicone foam as an implant material, but can also be produced by injection-molding-like methods)

Shapes: (depending on tumor bed size in diameter a=1, 2, 3, 4 and 5 cm)

2D or 3D star or

Spiral (similar to the spiral of the Somatex lung marker/ BioZorb) or

Spiral band/string (if same profile is consistently selected, the implant could optionally be removed by means of minor surgical intervention)

Radiopaque by:

small metal parts, optionally tantalum, gold, etc. or addition of $BaSO_4$ or other admixtures to the silicone base composition prior to polymerization Implementation Idea:

For example, a 3D silicone star composed of four prongs oriented in such a way that the distance between each of the four tips is the same (this could possibly make the radiotherapy planning simpler). Radiopaque markers are attached to the tips, which serve as a reference for the irradiation planning and allow 3D orientation. The silicone ensures that the star is not palpable in the breast postoperatively. In addition, the marker is available in different sizes (depending on the size of the tumor bed). In order to prevent migration of the marker, the star is attached (at its tips) to the margin of the tumor bed.

b.) Hydrogel as a Basic Material:

(only as a slowly resorbable variant with a low quelling factor, optionally based on PMMA or cytosan)

Shapes: (depending on tumor bed size in diameter a=1, 2, 3, 4 and 5 cm)

2D or 3D star of

Spiral (similar to the spiral of the Somatex lung marker/ BioZorb) or

Spiral band/string

Radiopaque by:

small metal parts, optionally tantalum, gold, etc. or addition of $BaSO_4$ or other admixtures Implementation Concept:

See example of silicon esters, only with hydrogel

Drawing of the Product Concept:

FIGS. 22a) to 22)d

The invention claimed is:

1. A marker body for marking breast tissue, the marker body comprising:

an at least partially tubular body made from a soft elastic material; and multiple radiopaque marker elements, the multiple radiopaque marker elements being carried by the at least partially tubular body, wherein the at least partially tubular body is configured to provide minimal resistance to an external, deforming force and return to an original shape of the at least partially tubular body in the absence of the external, deforming force, wherein the at least partially tubular body has two free longitudinal ends which are configured to be connected to each other to form an exterior portion of the marker body, the exterior portion defining an outermost diameter of the marker body and encompassing an interior space, and wherein the multiple radiopaque marker elements are configured as metal cylinders having a length and a diameter of less than 5 mm and are either inserted into a lumen of the at least partially tubular body or are pressed onto the at least partially tubular body from outside.

2. The marker body as claimed in claim 1, wherein, when the outermost diameter of the marker body is 3 cm, the at least partially tubular body is configured to resist an external force with an elastic force of less than 1 N on a 1 mm compression path.

3. The marker body as claimed in claim 1, wherein one of the two free longitudinal ends of the at least partially tubular body is configured to be plugged into the other of the two free longitudinal ends of the at least partially tubular body.

4. The marker body as claimed in claim 1, wherein at least one of the free longitudinal ends of the at least partially tubular body has a lumen which is configured to receive another free longitudinal end of the at least partially tubular body in order to detachably connect the two free longitudinal ends of the at least partially tubular body to each other.

5. The marker body as claimed in claim 1, wherein one of the two free longitudinal ends of the at least partially tubular body is at least slightly enlarged compared to the other of the two free longitudinal ends of the at least partially tubular body and is configured receive and clamp onto the other of the two free longitudinal ends via an elastic restoring force.

6. The marker body as claimed in claim 1, wherein the at least partially tubular body has a continuous lumen, or two or more lumens that, when taken together, extend over more than half of a total length of the at least partially tubular body.

7. The marker body as claimed in claim 1, wherein, in an initial straight state of the at least partially tubular body, the two free longitudinal ends are in a relaxed state, the at least partially tubular body extending only between the two free longitudinal ends along a singular longitudinal axis, and wherein, in a secondary state of the at least partially tubular body, the two free longitudinal ends are connected to each other such that the marker body comprises an elastic ring having a circular shape.

8. The marker body as claimed in claim 1, wherein the at least partially tubular body is composed of a soft bioresorbable polymer.

9. The marker body as claimed in claim 8, wherein the soft bioresorbable polymer is configured such that it is stable for at least 6 months in tissue and is then resorbed.

10. The marker body as claimed in claim 1, wherein the radiopaque marker elements are arranged at a uniform distance from one another on the at least partially tubular body.

11. The marker body as claimed in claim 1, wherein a total length of the at least partially tubular body is between 7.5 cm and 30 cm.

12. The marker body as claimed in claim 1, wherein the two free longitudinal ends of the at least partially tubular body are configured to be connected by inserting one of the two free longitudinal ends into the other of the two free longitudinal ends.

13. The marker body as claimed claim 1, wherein the two free longitudinal ends of the at least partially tubular body have the same diameter and are configured to be plugged together via a connecting element.

14. The marker body as claimed in claim 13, wherein the connecting element is composed of a bioresorbable plastic that is harder than a material from which the at least partially tubular body is formed.

15. The marker body as claimed in claim 13, wherein the connecting element is a metal connecting pin that serves as one of the radiopaque marker elements.

16. The marker body as claimed in claim 1, wherein the at least partially tubular body has eyelets or loops such that the marker body may be stitched into an area from which a tumor has been removed to prevent migration of the marker body.

17. The marker body as claimed in claim 1, wherein the marker body is composed of multiple at least partially tubular bodies that are connected to each other at their respective longitudinal free ends.

18. The marker body as claimed in claim 1, wherein the at least partially tubular body has predetermined break points at which the at least partially tubular body can be manually shortened without using a tool.

19. The marker body as claimed in claim 1, wherein the at least partially tubular body has a loop at each of the two free longitudinal ends through which the at least partially tubular body may be guided to form the exterior portion of the marker body that is adjustable in diameter.

20. The marker body as claimed in claim 1, wherein the marker body is configured to mark an area from which a tumor has been removed for radiotherapy.

21. The marker body as claimed in claim 1, wherein the two free longitudinal ends are configured to be directly connected to each other in an end-to-end configuration.

22. The marker body as claimed in claim 8, wherein the at least partially tubular body is composed of polylactic acid (PLA), poly-l-lactic acid (PLLA), polyglycolic acid, poly-caprolactone, poly-p-dioxanone, ε-caprolactone, or Evonik Resomer.

23. The marker body as claimed in claim 10, wherein the multiple radiopaque marker elements are arranged at a distance of between 1 cm and 3 cm from each other.

24. The marker body as claimed in claim 1, wherein, when the two free longitudinal ends are detachably connected to each other, a connection between the two free longitudinal ends is configured to be detached through application of an external force of greater than 2 N.

25. A marker body for marking breast tissue, the marker body comprising:

an at least partially tubular body made from a soft elastic material; and multiple radiopaque marker elements, the multiple radiopaque marker elements being carried by the at least partially tubular body, wherein the at least partially tubular body is configured to provide minimal resistance to an external, deforming force and return to an original shape of the at least partially tubular body in the absence of the external, deforming force, and wherein the at least partially tubular body has two free longitudinal ends which are configured to be connected to each other to form an exterior portion of the marker body, the exterior portion defining an outermost diameter of the marker body and encompassing an interior space, and wherein each of the two free longitudinal ends of the at least partially tubular body has a loop through which the at least partially tubular body may be guided to form the exterior portion of the marker body that is adjustable in diameter.

* * * * *